(12) United States Patent
Kovtoun

(10) Patent No.: US 8,581,177 B2
(45) Date of Patent: Nov. 12, 2013

(54) HIGH DUTY CYCLE ION STORAGE/ION MOBILITY SEPARATION MASS SPECTROMETER

(75) Inventor: Viatcheslav V. Kovtoun, Santa Clara, CA (US)

(73) Assignee: Thermo Finnigan LLC, San Jose, CA (US)

(*) Notice: Subject to any disclaimer, the term of this patent is extended or adjusted under 35 U.S.C. 154(b) by 175 days.

(21) Appl. No.: 13/084,304

(22) Filed: Apr. 11, 2011

(65) Prior Publication Data
US 2012/0256083 A1  Oct. 11, 2012

(51) Int. Cl.
*H01J 49/00* (2006.01)

(52) U.S. Cl.
USPC ............ 250/281; 250/282; 250/283

(58) Field of Classification Search
USPC ........................................ 250/281
See application file for complete search history.

(56) References Cited

U.S. PATENT DOCUMENTS

| | | | |
|---|---|---|---|
| 5,847,386 A * | 12/1998 | Thomson et al. | 250/288 |
| 6,498,342 B1 * | 12/2002 | Clemmer | 250/287 |
| 7,560,688 B2 * | 7/2009 | Clowers et al. | 250/287 |
| 7,718,959 B2 | 5/2010 | Franzen et al. | |
| 2007/0114382 A1 * | 5/2007 | Clemmer et al. | 250/287 |
| 2009/0173877 A1 | 7/2009 | Bateman et al. | |

FOREIGN PATENT DOCUMENTS

| | | |
|---|---|---|
| EP | 1 505 632 A1 | 2/2005 |
| EP | 1 505 635 A2 | 2/2005 |

* cited by examiner

*Primary Examiner* — Phillip A Johnston
(74) *Attorney, Agent, or Firm* — Michael C. Staggs

(57) ABSTRACT

A novel high ion storage/ion mobility separation mass spectrometer that provides for a high duty cycle of operation is presented herein. In particular, the example embodiments, as disclosed herein, provides for a high ion storage/ion mobility instrument that beneficially includes a two-dimensional (2D) plurality of adjacently arranged ion confinement channels to provide a high storage bank of a desired mass range of ions. Such ions, via ion mobility transport, are separated into smaller fractions of an overall mass window into desired confinement regions of the disclosed 2D confinement channels and thereafter transferred out in a manner so as to enable the aforementioned novel high-duty cycle of sequential operation.

20 Claims, 3 Drawing Sheets

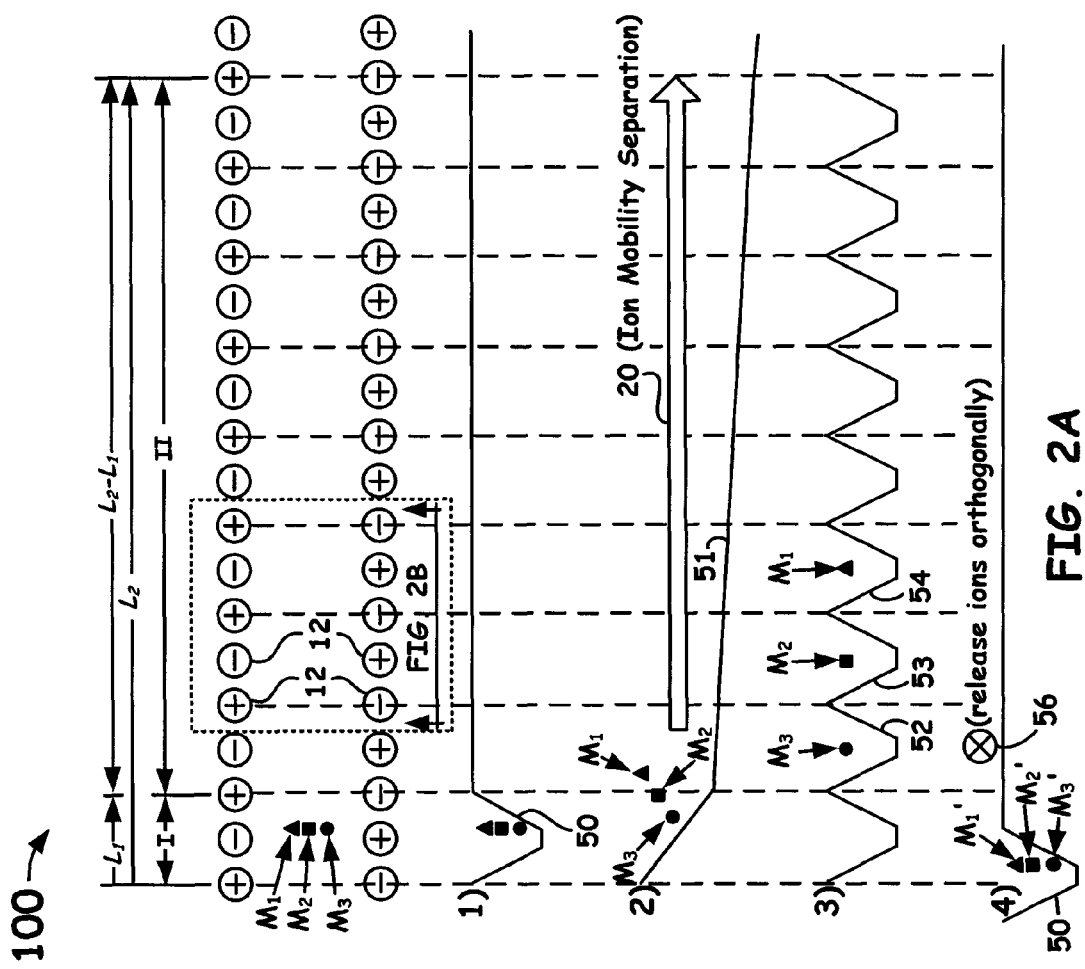
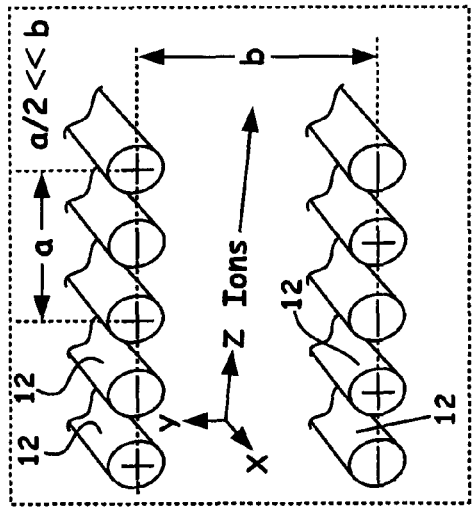
FIG. 2A
FIG. 2B

HIGH DUTY CYCLE ION STORAGE/ION MOBILITY SEPARATION MASS SPECTROMETER

BACKGROUND OF THE INVENTION

1. Field of the Invention

The present invention relates to the field of mass spectroscopy. More particularly, the present invention relates to the field of mass spectroscopy directed to a novel system and method that enables combining ion storage and ion mobility separation on the same time scale so as to provide high duty cycle analysis of the collected ions.

2. Discussion of the Related Art

High-throughput refers to a technology in which a large number of measurements can be taken in a fairly short time period. "Ome" and "omics" are suffixes that are derived from genome (the whole collection of a person's DNA) and genomics (the study of the genome). High-throughput analysis is essential when considering data at the "omic" level, that is to say considering all DNA sequences, gene expression levels, or proteins at once. Without the ability to rapidly and accurately measure tens and hundreds of thousands of data points in a short period of time, there is no way to perform analyses at this level. In particular, high-throughput analysis in various OMICS' requires a high duty cycle of operation, often by using a configured mass spectrometer. This requires that mass analysis be done faster than ion accumulation or the ions desired to be interrogated must be stored in a manner that enables spectral quality mass analysis. With ever increasing of brightness of the ion sources, the second approach is beneficial.

To provide such ion storage with mass analysis creates a need for higher storage capabilities of the ions. Relative high capacity storage of ions in the field of mass spectroscopy presently entails configurations of linear RF multipole rod assemblies, more often quadrupole arrangements, wherein phases of an applied RF voltage are alternatively applied to opposing rod pairs. From such an arrangement, a pseudo potential is created that enables accelerating the ions in the interior of the device towards the axis so as to enable oscillations around the potential minimum along the length of the interior axis. Applied DC fields located at the ends of the rod poles or applied to predetermined sections of the rods enables trapping of desired ions. Moreover, such devices can also be provided with a buffer inert gas, e.g., Helium, Neon, Argon, to assist the ions in losing their initial kinetic energy via low energy collisions. In the right configuration, introduction of such gases also enables different ion species to be separated by their ion mobility, i.e., by ion mobility spectrometry (IMS).

The utility of ion mobility spectrometry (IMS) for separation of ions has been demonstrated extensively, but IMS combined with mass spectrometry (MS) has remained a niche technique, mainly because of the loss of sensitivity due to ion losses within the combination of techniques. IMS, in particular, remains a desired technique to be coupled with MS because of the speed of the separation technique. Specifically, IMS exploits the beneficial aspect that different particles diffuse through a gas at different speeds, depending on their collision cross-sections with the introduced gas molecules. While neutrals diffuse randomly (via Brownian motion), ions in an applied electric field drift in a defined direction with the velocity controlled by their mobility (K). Such a quantity generally varies with the field intensity E but IMS is often run in a low-field regime where K (E) is substantially constant. In that limit, K depends on the ion/buffer gas collision cross-section $\Omega$, of which allows a spatial separation of different ions.

Accordingly, a need exists for providing higher ion storage configurations that capitalize primarily on ion mobility separation to provide high duty cycle analysis of the collected ions. The present embodiments, as disclosed herein, addresses this need by providing novel arrangements designed to confine desired high ion loads in groups after ion mobility separation and can be directed to scan out desired groups of ions to coupled analyzers while continually filling storage region(s).

Background information on an ion storage bank system is described and claimed in U.S. Pat. No. 7,718,959 B2, entitled, "STORAGE BANK FOR IONS," issued May 18, 2010, to Frantzen et al., including the following, "[t]he invention relates to instruments for storing ions in more than one ion storage device and to the use of the storage bank thus created. The ion storage bank includes several storage cells configured as RF multipole rod systems, where the cells contain damping gas and are arranged in parallel. Each pair of pole rods is used jointly by two immediately adjacent storage cells such that the ions collected can be transported from one storage cell to the next by briefly applying DC or AC voltages to individual pairs of pole rods. The ions can thus be transported to storage cells in which they are fragmented or reactively modified, or from which they can be fed to other spectrometers. In particular, a circular arrangement of the storage cells on a virtual cylindrical surface makes it possible to accumulatively fill the storage cells with ions of specific fractions from temporally sequenced separation runs."

Background information for a mass spectrometer system that incorporates a 2-D "traveling wave" ion guide for moving trapping regions along the ion guide, is described and claimed in, EP No. 1 505 632 A1, entitled, "MASS SPECTROMETER," published Feb. 9, 2005, to Bateman et al., including the following, "[a] mass spectrometer is disclosed wherein ions from a pulsed ion source 10, 11 are dispersed in a drift region 16 so that the ions become separated according to their mass to charge ratios. The ions are then received by an ion guide 1 in which multiple trapping regions are created and wherein the multiple trapping regions are translated along the length of the ion guide 1. The ion guide 1 receives the ions so that all the ions trapped in a particular trapping region have substantially the same or similar mass to charge ratios. The ions are released from the exit of the ion guide 1 and the pusher/puller electrode 14 of an orthogonal acceleration Time of Flight mass analyzer is arranged to be energized in synchronization with the ions emerging from the ion guide 1; The trapping regions may be translated along the ion guide 1 with a velocity which becomes progressively slower and the delay time of the pusher/puller electrode 14 may be progressively increased."

Another exemplary source of background material for 2D-guides using stacked plates or rings arranged parallel and generally transverse to the travel axis of ions can be found in (See Gerlich et al, (1992): Inhomogeneous Electrical Radio Frequency Fields: A versatile tool for the study of processes with slow ions. Adv. In Chem Phys LXXXII, 1. ISBN 0-471-53258-4, John Wiley and Sons). Generally, such structures are also arranged as radio frequency (RF) ion guides and operated under elevated pressures to efficiently transmit ions from one portion of a spectrometer to another. These devices work on the principle of so called "effective potential wells" that can trap the ions in these wells for extended periods of time either by the use of cylindrical geometry devices such as conventional Paul traps, or using linear geometry devices such as multipole guides or ring sets with end plates providing a trapping D. C. potential.

SUMMARY OF THE INVENTION

The present invention is directed to a novel high duty cycle ion storage/ion mobility mass spectrometer that includes: an ion source; a first ion interface instrument partitioned into one or more confinement channels having predetermined spatial locations provided by desired DC and RF potentials, wherein a first confinement channel of the first ion interface instrument is configured to receive ions of a predetermined mass window from the ion source and adjacent one or more confinement channels ($N_1$) configured within the first ion interface instrument is designed to, via ion mobility transport, receive and thereafter confine selected ions of a smaller fraction of the mass range of the predetermined mass window; a second ion interface instrument additionally partitioned into one or more confinement channels ($N_2$) also having predetermined spatial locations provided by desired DC and RF potentials, wherein any of the one or more confinement channels ($N_2$) is configured to receive from said one or more confinement channels ($N_1$) configured within said first ion interface instrument, said selected ions of a smaller fraction of the mass range of said predetermined mass window, said second ion interface instrument being additionally configured to transfer such selected ions to successive ion confinement channels; and one or more mass analyzers having an entrance configured to receive ions transferred from one or more predetermined confinement channels of the second ion interface instrument to enable high throughput mass analysis.

A second aspect of the present invention is directed to a method of mass spectrometric analysis that includes: a) providing an ion interface instrument partitioned into a first confinement channel and adjacent one or more confinement channels ($N_1$), each of which has predetermined fixed spatial locations configured from desired DC and RF potentials, b) providing a packet of ions of a predetermined mass window into the first confinement channel; c) releasing ions of the predetermined mass window from the first confinement channel and locking fractions of the ions into predetermined the adjacent one or more confinement channels ($N_1$) after urging, via ion mobility separation and transport, into the predetermined adjacent one or more confinement channels ($N_1$); d) providing a subsequent packet of ions of the predetermined mass window into the first confinement channel after the transfer of the fractions of the ions of the predetermined mass window into the adjacent one or more confinement channels ($N_1$) configured within the ion interface instrument; e) transferring one or more of more of the fractions of ions of the predetermined mass window to an entrance of one or more mass analyzers; f) mass analyzing the ions of the predetermined mass window; g) repeating steps c) to f); for any number of a plurality of the subsequent packet of ions of a predetermined mass window, wherein the packet of ions have a mass-to-charge window similar to a mass-to-charge window of any of the subsequent packet of ions.

Accordingly, the novel high ion storage/ion mobility separation mass spectrometer, as disclosed herein, provides for a high duty cycle of operation via, in particular, a beneficial high ion storage/ion mobility instrument to result in a significant dynamic range improvement of a given mass range and with an ion mobility resolution of down to about 10.

BRIEF DESCRIPTION OF THE DRAWINGS

FIG. 2A shows an orthogonal view of the 2D high ion storage/ion mobility confinement interface instrument and corresponding schematic applied DC fields to predetermined electrodes.

FIG. 2B shows an exploded view of a portion of the 2D high ion storage/ion mobility confinement interface instrument for clarification of aspects of the instrument.

DETAILED DESCRIPTION

Figure 1:
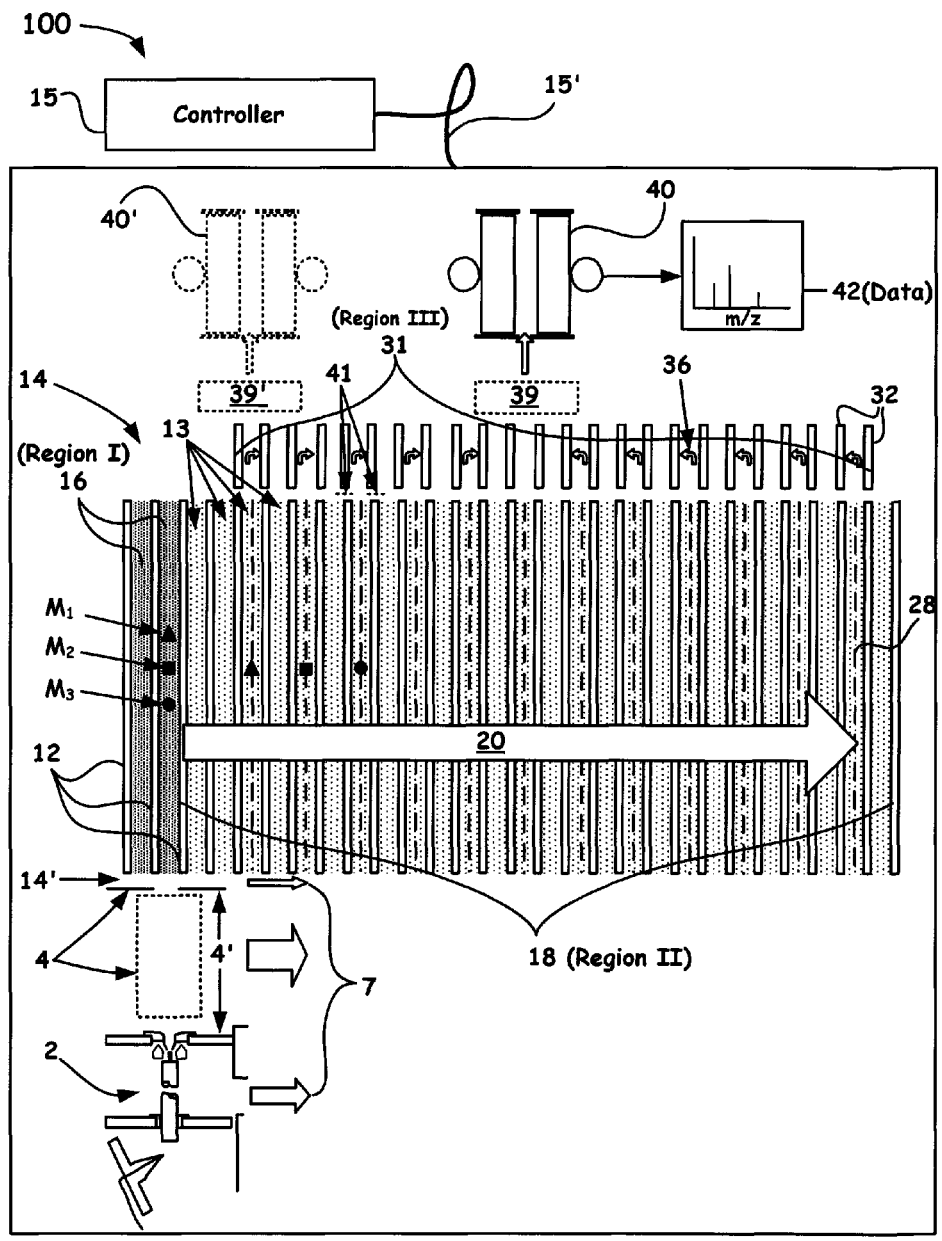
FIG. 1 shows a beneficial example High Duty Cycle Ion Storage/Ion mobility mass spectrometer.

In the description of the invention herein, it is understood that a word appearing in the singular encompasses its plural counterpart, and a word appearing in the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. Moreover, it is to be appreciated that the figures, as shown herein, are not necessarily drawn to scale, wherein some of the elements may be drawn merely for clarity of the invention. Also, reference numerals may be repeated among the various figures to show corresponding or analogous elements. Additionally, it will be understood that any list of such candidates or alternatives is merely illustrative, not limiting, unless implicitly or explicitly understood or stated otherwise. In addition, unless otherwise indicated, numbers expressing quantities of ingredients, constituents, reaction conditions and so forth used in the specification and claims are to be understood as being modified by the term "about."

Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

General Description

With respect to ion traps, the ability to see low abundant complex mixtures together with high abundant components of complex mixtures together with high abundant ions and high levels of background ions is restricted by the ion capacity of the particular device in use. As a basic premise, the total ion population desired to be stored in the trapping device should not exceed some threshold value ($C_T$), which is a figure of merit value that relates to the allowable analytical ion capacity of the instrument. It is important to note that above this $C_T$ value for a particular device, the spectral quality across a desired mass range begins to decline.

Accordingly, the present invention is directed to addressing this basic threshold ion storage limitation via a system and method that combines high ion storage and ion mobility separation on the same time scale so as to result in a novel system that enables a high duty cycle of operation. In particular, the present invention provides for a method and system of mass spectrometry wherein a high ion storage/ion mobility instrument is disposed as an interface between an ion source inlet and a mass analyzer.

The high ion storage instrument itself is generally configured as a two-dimensional (2D) plurality of sequentially arranged ion confinement regions to provide the desired high ion storage capability of a desired mass range of ions. To enable the requisite $C_T$ for the interface instrument, the beneficial confinement regions are configured from an array of elongated electrodes having their major axis oriented transversely to the overall direction of the ion movement through the device.

Specifically, the 2D arrangement of confinement regions enables ions allowed within the device to be spread over the array, with each confinement region holding ions for mass analysis being only a fraction of the whole mass range of interest. Confinement in addition to transport and separation of predetermined ions (including ions of opposite polarity) is accomplished by application of predetermined radio-frequency (RF) and direct current (DC) voltages to the rod electrodes themselves and/or to desired ion optical structures (e.g., end plates, apertured lenses, auxiliary electrodes, etc.).

Accordingly, a basis of the present invention is directed to providing applied static DC confinement fields and gradients (e.g., descending or ascending gradients) for ion mobility separation and transport into one or more predetermined spatial locations is presented. Such ions confined in the groups (selected mass ranges held in predetermined confinement regions) after ion mobility separation are thereafter directed to be scanned out of their sequential locations, as disclosed herein, while new ions continue filling storage regions so as to enable the novel high-duty cycle of operation as disclosed herein.

Specific Description

FIG. 1 illustrates an example mass spectrometer, generally designated by the reference numeral 100, configured to operate according to aspects of the configurations disclosed herein. While the system 100 of FIG. 1A is beneficial for illustrative purposes, it is to be understood that other alternative commercial and custom configurations and having various other components, as known and as understood by those in the field of mass spectroscopy, can also be incorporated when using the 2D high ion storage/ion mobility confinement interface instrument and disclosed coupled instruments.

Thus, as shown by the general example system 100 of FIG. 1, the system generally includes an ion continuous source 2, ion transfer optics 4, a 2D high ion storage/ion mobility confinement interface instrument 14 that comprises labeled storage Regions I 16 and II 18, a region (i.e., Region III 31) having a plurality of ion mobility buckets 36, one or more analyzers 40, and a controller 15, as known and understood by those skilled in the art.

From such an arrangement, a sample containing one or more analytes of interest can be ionized via ion source 2 using any of the applicable techniques known and understood by those of ordinary skill in the art. While FIG. 1 depicts an Electrospray Ionization (ESI) configuration as the example ion source 2, a variety of other configurations to provide ions of interest can also be incorporated, such as, but not limited to, Atmospheric Pressure Ionization (API), Atmospheric Pressure Chemical Ionization (APCI), Nanoelectrospray Ionization (NanoESI), thermospray ionization, electron impact (EI) ionization, chemical ionization (CI) source, an EI/CI combination ionization source or any other source that can be utilized without departing from the scope of the invention. In addition, while FIG. 1 generally shows a Linear Ion trap (LIT) as an example analyzer 40 configured therein, the mass analyzers 40, as disclosed herein, may nonetheless may be of any type of single or multiple stage analyzer, including, but not limited to, quadrupole mass analyzers, two dimensional ion traps, three dimensional ion traps, electrostatic traps, time-of-flight (TOF) devices, and/or Fourier Transform Ion Cyclotron Resonance analyzers. As another example but beneficial arrangement, the analyzer itself can include an array of analyzers, e.g., 40, 40' of any of the aforementioned types (only two shown for simplicity with 40' being shown in dashed representation), configured to each collect from a single channel from Region III 31, as shown in FIG. 1, or even from groups formed from a plurality of channels (not shown) similar to the arrangement described below for a single analyzer 40 embodiment of FIG. 1. Using such an arrangement also allows the systems and methods described herein to operate in a high-resolution mode even where fragmented ions introduced into channels of Region III 31 are utilized, as described below.

It is also to be appreciated that the operation of mass spectrometer 100 is enabled by the controller and data system (generally referenced by the numeral 15 as coupled to system 100 via an interface 15') of various circuitry of a known type. Such a control and data system can be implemented as any one of or a combination of general or special-purpose processors (digital signal processor (DSP)), firmware, software, and/or hardware circuitry to provide instrument control, RF and DC power, and data analysis, etc., for the example configurations disclosed herein.

It is also to be appreciated that instructions to operate the system shown in FIG. 1, which includes the enabling of desired RF and DC voltages, the control of pressure via pumping means known in the art, the identifying of m/z values (e.g., data 42), the merging of data, the exporting/displaying/outputting to a user of results, etc., may be executed via a computer based system (e.g., an extension of controller 15) which includes hardware and software logic for providing the instructions and control functions of the mass spectrometer 100.

In addition, such instructions and control functions, as described above, can also be implemented by a mass spectrometer system 100, as shown in FIG. 1, configured to operate via a machine-readable medium (e.g., a computer readable medium). A computer-readable medium, in accordance with aspects of the present invention, refers to media known and understood by those of ordinary skill in the art, which have encoded information provided in a form that can be read (i.e., scanned/sensed) by a machine/computer and interpreted by the machine's/computer's hardware and/or software.

A novel part of the embodiment shown in FIG. 1 entails the configuration itself of the 2D high ion storage/ion mobility confinement interface instrument 14. The top-down symbolic view of FIG. 1 shows the 2D interface instrument 14 as generally comprising two sections, which are depicted as Region I 16 and Region II 18, with Region III 31 utilized for adjacent ion packet transport so as to be interrogated by analyzer 40, as to be discussed in detail herein. It is thus to be noted that Region I 16 plus Region II 18 in combination with Region III 31 form a pair of separate ion interface instruments.

Region I 16 and Region II 18 are in essence a plurality of separate confinement cells 13 (of up to about 20 channels) configured from pairs of elongated electrodes 12 that cooperate with ion mobility transport and separation techniques for predetermined ions. It is to be appreciated that the use of elongate rods in Regions I 16 and II 18 is beneficial for ion mobility separation, as disclosed herein; otherwise space charge interaction may adversely affect mobility resolution.

When operating the example instrument 100 of FIG. 1, it is beneficial that the electrodes 12 are electrically isolated from one another so as to enable radio-frequency (RF) voltages to be applied to the electrodes 12 (as directed by controller 15 and interface 15') in a designed adjustable 180 degrees out of phase and/or amplitude relationship to the alternating rods (denoted by the + and − notations at the ends of electrodes, as shown in FIGS. 2A and 2B). Rod geometries can include hyperbolic, flat, but preferably round electrode structures. Along with the aforementioned applied RF voltage(s), the electrodes 12 can also be coupled with DC confining voltages or predetermined descending or ascending DC voltages, using methods disclosed herein, to also create an axial DC electric field along the Z-Axis illustrated in FIG. 2B so as to aid transport of desired mass ranges of ions via ion mobility physics. When desired, such DC gradient voltages to aid ion mobility transport and separation or ejection into corresponding regions (i.e., from region II 18 into region III 31) can also be provided by auxiliary electrode structures 28, as generally shown in FIG. 1 and as detailed below. As another arrangement, containment and/or DC potential gradients can be provided by configured plate electrodes residing above and/or below rod configurations (not shown), as known and as understood by those skilled in the art.

Moreover, as an additional embodiment, each electrode 12 and 32 shown in Regions I 16 and II 18 and III 31 can be configured as segmented rods having a front end, central and back end segments, which are also electrically isolated from each other to allow each segment to be maintained at a different DC potential. For example, the DC potentials applied to the front end and back end sections may be raised relative to the DC potential applied to the central sections to create a potential well that axially confines positive ions to the central portion of any predetermined confinement channel. It is also to be appreciated that each electrode 12 and 32 can also be configured as a multiple segmented rod that provides a larger number of segmented sections than that described above to provide more precise DC potentials along the length of the rod segments for containment as well as for urging ions in a predetermined direction, e.g., towards Region III 31 from Region II 18.

Generally, Region III 31, as generally stated above, forms a second ion interface instrument that includes a plurality of configured confinement cells (channels) arranged from shorter electrode structures 32 adjacent to each other such that ions 36 of a smaller designed mass range (i.e., ion buckets that are a fraction of an overall desired mass window) received from one or more confinement channels of Region II 18 can be transferred between adjacent confinement cells (channels) so as to be interrogated by analyzer 40.

Region III 31 that forms the second ion interface instrument is designed to receive respective groups of ions 36 from individual channels 13 directed from Region II 18, and can, when directed, transport such ions to an inlet of analyzer 40 via a series of successive transfers between adjacent confinement cells. It is also to be noted that when the analyzers 40, 40' are configured as a plurality (e.g., as an array), the ions can also be held within each confinement channel within Region III 31 after undergoing collision/reaction in a device (not shown) configured before one or more of the channels shown for Region III 31. Moreover, Region III 31 also provides for desirable ion optics and structural configurations, as generally shown in FIG. 1 via dashed boxes 39, 39' (only two shown for simplicity) and general dashed markings 41 (again only two shown for simplicity). Such ion optics and structural configurations thus enable the manipulation of ions (containing and directing) for each channel and to provide a desirable working environment for Region III 31 that includes enabling gas (e.g., Nitrogen, Argon) pressures ranging from about 0.2 torr up to about 2 mtorr.

Desirably thereafter, transfer to a respective analyzer, e.g., 40, 40', can take effect so as to handle larger m/z ranges as a consequence of fragmentation without appreciably affecting the high-duty cycle of operation of the embodiments disclosed herein. It is also to be noted that since light ions traverse the length of the Region II 18, e.g., note arrow 20 in FIG. 1, sequential timing and operation is often desirably provided to first direct such lighter ions (e.g., $M_3$, as shown in FIG. 1) ending with the heavier ions (e.g., $M_1$, also as shown in FIG. 1) to be transferred to Region III 31 so as to thereafter be transferred and interrogated by analyzer 40.

Similar but somewhat different to the means provided for Region II 18, confinement of predetermined ions 36 within defined confinement channels can be achieved by the combined action of oscillatory (e.g., RF) and static fields effected by the application of desired voltages (RF and DC) to electrodes 32 (including segmented electrodes) of Region III 31. Confinement along the long axis of electrodes 32 that provide such confinement channels is enabled by repulsive DC and RF potentials applied to known electrode structures at segmented portion, as similarly described above, and/or at opposing ends (not shown for simplicity) of such confinement channels. Gas pressure of about 20 mtorr up to about 100 motor within Region III 31 is designed to aid in radial confinement without causing undesired fragmentation effects.

When transfer of ions is desired in Region III 31, predetermined voltages are adjusted or removed in order to eliminate potential barriers between adjacent confinement regions so as to urge ions to the next (i.e., adjacent) confinement cell and the method is repeated so as to be eventually received by the aforementioned analyzer 40. Axial DC field gradients can also be utilized to aid ion movement by providing desired DC potentials to desired electrodes 32 or by providing desired DC gradients via disposed auxiliary electrodes (not shown), as similarly discussed below for the configuration in FIG. 3B. It is desirable to perform the transfers as quickly as possible, and more particularly on a time scale that is short compared to the scan-out window period. The result is a data 42 having a desired spectral quality due to the increase in dynamic range provided by the mass spectrometer 100 of FIG. 1.

FIG. 2A and FIG. 2B show an orthogonal view of Region I 16 and Region II 18 (as also denoted with bi-directional arrows) and the reader is directed to such illustrations to gain a further appreciation of the novelty of the 2D high ion storage/ion mobility confinement interface instrument 14 portion with respect to such regions. In particular, FIGS. 2A and 2B are utilized in combination with FIG. 1 to better illustrate the configured confinement cells of Region I 16 and Region II 18, as enabled by the plurality of pairs of axially elongated electrodes 12. (Also note: for this example configuration, three multipoles provide individual confinement channels due to imposed DC potentials, as generally shown by the dashed lines in FIG. 2A, as to be discussed herein).

The dashed box within FIG. 2A to correspond to the expanded view in FIG. 2B illustrates a preferable rod configuration and denoted phase relationship (+ and − notations) to enable the pseudo potential barriers and thus the potential minima along the Z-axial direction of the instrument shown in FIG. 1. Specifically, by configuring the separation of the electrode rods along the Y axis (i.e., corresponding to the labeled electrode rod separation "b" in FIG. 2B) to be substantially greater than an inter-rod separation distance labeled "a/2", e.g., wherein the labeled separation "b" is preferably 2-3 times greater than the inter-rod separation "a/2", as shown in FIG. 2B, the ions of choice are easily axially contained by the resultant RF pseudo potentials with applied DC axial fields and ion mobility separation techniques being the means to move desired ions transversely to any one of confinement channels along the labeled Z-axis, as shown in FIG. 2B. Thereafter, applied DC fields, as discussed below, enable confinement within predetermined confinement channels.

In operation while referencing FIG. 1 and FIG. 2A, ions having different m/z values, e.g., generally labeled as $M_1$, $M_2$, and $M_3$ (shown respectively as a triangle, square, and circle) generated by ion source 2 (e.g., an ESI source) can be directed via ion transfer optics 4 (e.g., an aperture ion lens, an S-lens 150 (the design and operation of which is described in U.S. Pat. Nos. 7,514,673 and 7,781,728 to Senko et al., electrostatic lenses, etc) so as to first fill Region I 16 of the 2D high ion storage/ion mobility confinement interface instrument 14 up to its limit (e.g., $N*C_T$). FIG. 1 also generally shows one or more different pressurized regions 7 (as also denoted by the thicker directional arrows). It is to be appreciated, however, that the ion transfer optics 4 portion 4' (denoted with double directional arrows) is often desirably provided with a pressure ranging from about 1 mtorr up to about 4 motor in contrast to a decoupled pressure region 14' (i.e., configured for pressures ranging from about 20 mtorr up to about 100 motor) that provides the working environment for the 2D high ion storage/ion mobility confinement interface instrument 14.

In operation therefore, the 2D high ion storage/ion mobility confinement interface instrument 14 comprising Regions I and II, as shown in FIG. 1, is often filled to the aforementioned gas (e.g., Helium, Neon, Argon) pressures ranging from about 20 mtorr up to about 0.1 torr while under the influence of an applied DC field gradient (e.g., via DC pulses ranging from about 1 volt/cm up to about 10 volts/cm). Such example applied DC field gradients and beneficial pressures enable ion mobility physics to apply to the ion transport (e.g., in a time frame of less than about 200 microseconds (μsec)) and separation (denoted as reference numeral 20 in FIGS. 1 and 2A) of the ions that are evenly distributed in Region I into desired (not necessarily adjacent) one or more confinement channels. In addition, such a pressure also operates as a damping means to aid in confinement to the interior of each of the configured channels but without deleterious fragmentation effects.

It is to also be appreciated that while not shown in FIG. 1, repulsive RF and/or DC pulses applied to electrode structures known by those skilled in the art (end plates, aperture lenses, etc.), are employed at opposing ends of each confinement channel to prevent desired ions coming close to such lenses from passing when not directed to do so.

Turning now specifically to the bottom of FIG. 2A, such steps labeled 1), 2), 3), and 4) schematically represent applied DC potentials acting in cooperation with applied RF potentials that enable confinement and transport of ions once a desired number within a given mass range have been evenly distributed into Region I at up to the limit (e.g., $N*C_T$), wherein N represents the number of confinement cells (sub-regions) that an overall desired mass range directed into Region I is to be divided into.

Accordingly, as shown in step 1) of FIG. 2A, the illustrative ions ($M_1$, $M_2$, and $M_3$) evenly distributed into Region I are first contained in the transverse direction (i.e., the Z-axis) via the DC potential well 50 enabled by applied DC voltages to predetermined electrodes in Region I (as denoted via corresponding dashed lines).

Step 2) indicates the movement of the ions $M_1$, $M_2$, and $M_3$, into Region II via application of desired DC electric field gradient 51 of about 1 V/cm up to about 10 V/cm by applied predetermined voltages (e.g., via DC pulses from about 1 μsec up to about 10 μsec and even in the tens of microseconds, e.g., up to about 40 μsecs) to selected electrodes (as also denoted with corresponding dashed lines). In particular, such example ions $M_1$, $M_2$, and $M_3$ move in the transverse direction 20 via ion mobility transport principles (e.g., mobility of ions and environment conditions) while under the influence of the illustrative configured DC electric field gradient 51 shown in FIG. 2A and the applied RF field (not indicated) that aids in confining the ions ($M_1$, $M_2$, and $M_3$) radial motion.

Step 3) shows that when separation is completed, ions ($M_1$, $M_2$, and $M_3$) can be locked into corresponding confinement channels via configured DC potential wells, e.g., 52, 53, and 54, by raising the DC potentials at selected electrodes (e.g., as denoted by the dashed lines) in a predetermined fashion.

Step 4) shows that upon separation, the DC potentials are reset and example ions $M_1$, $M_2$, and $M_3$ are ejected 56 (as also denoted by the direction marking indicating into the plane of the illustration) along the long axis of each confinement cell and into Region III 31 of mass spectrometer system 100 using applied DC potentials (e.g., using opposing DC end plates and aperture lenses) or DC gradients enabled by configured auxiliary electrodes 28. Beneficially while ions are being ejected 56 into Region III to enable scanning out desired groups of ions to a coupled analyzer(s) 40, ions can be continually filling Region I with new ions $M_1'$, $M_2'$, and $M_3'$, of a given desired mass range and the process can be repeated.

It is to be appreciated that the movement of ions across the 2D ion interface instrument 14 arrangement described herein and as described in step 2 above, can often provide for an uneven distribution of ions within each channel as a result of differential ion mobility characteristics of a given mass window. Thus, as an added arrangement, the example embodiments herein can also be provided with Automatic gain control (AGC) configurations and methods, as known to those skilled in the art, to control the number of ions to be directed out of the individual channels of the 2D ion interface instrument 14 into Region III 31 so as to be eventually characterized by a given analyzer 40, 40'. In operation, AGC can be incorporated by first injecting ions into an analyzer 40, 40', described herein, for some predetermined time from one or more individual confinement channels of the 2D ion interface instrument 14 shown in FIG. 1 using known in the art gating optical elements (not shown), typically in a pre-scan. A measurement of the resultant signal in the pre-scan is taken, and a calculation is then performed to determine what injection time (i.e. how long a gate is open for one or more desired confinement channels) is needed to yield a specified "target" amount of signal, the target being the optimum signal that provides the proportionate amount of a given fraction of ions of a predetermined desired overall mass window. The calculation to be utilized herein can often also use a simple linear relationship between ion signal and injection time.

It is also to be appreciated that utilized auxiliary electrodes can include a structure similar to that as described in U.S. Pat. No. 7,675,031 and as incorporated by reference in its entirety, or by providing a set of conductive metal bands spaced along predetermined rods with a resistive coating between the bands, providing resistive coatings with interposed insulators to tube structures, resistive or coated auxiliary electrodes that can also include interposed insulators, and/or other means known to one of ordinary skill in the art to move ions via induced DC axial forces along desired ion paths.

Figure 3A:
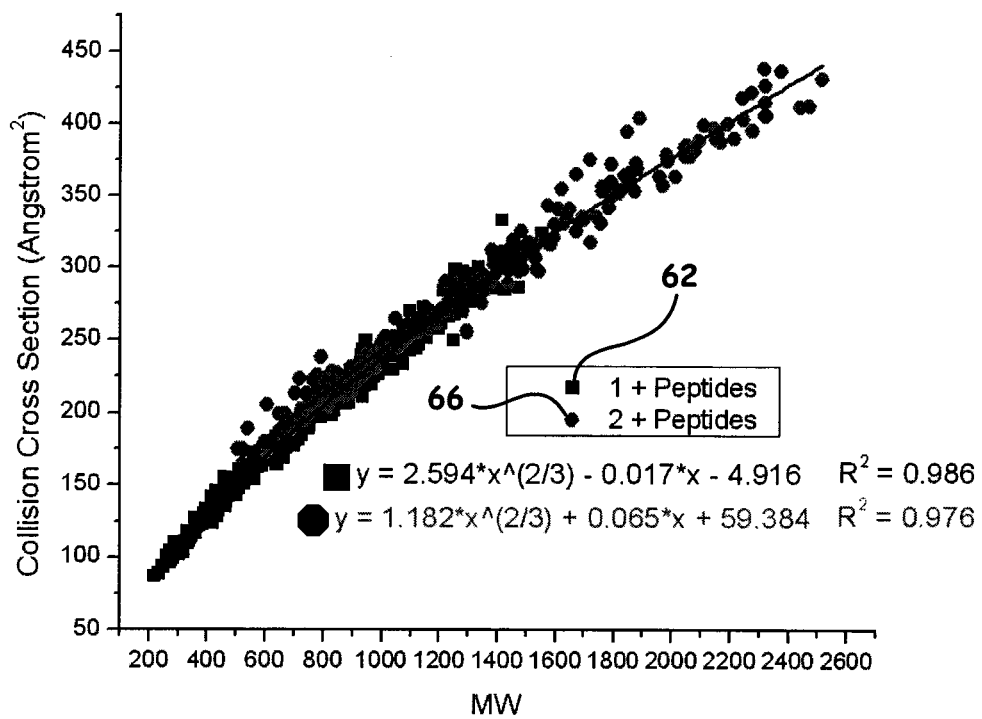
FIG. 3A shows the relationship between the collision cross-section measurements $\Omega$ ($\text{Å}^2$) of singly and doubly protonated proteins as a function of molecular weight (MW).
Figure 3B:
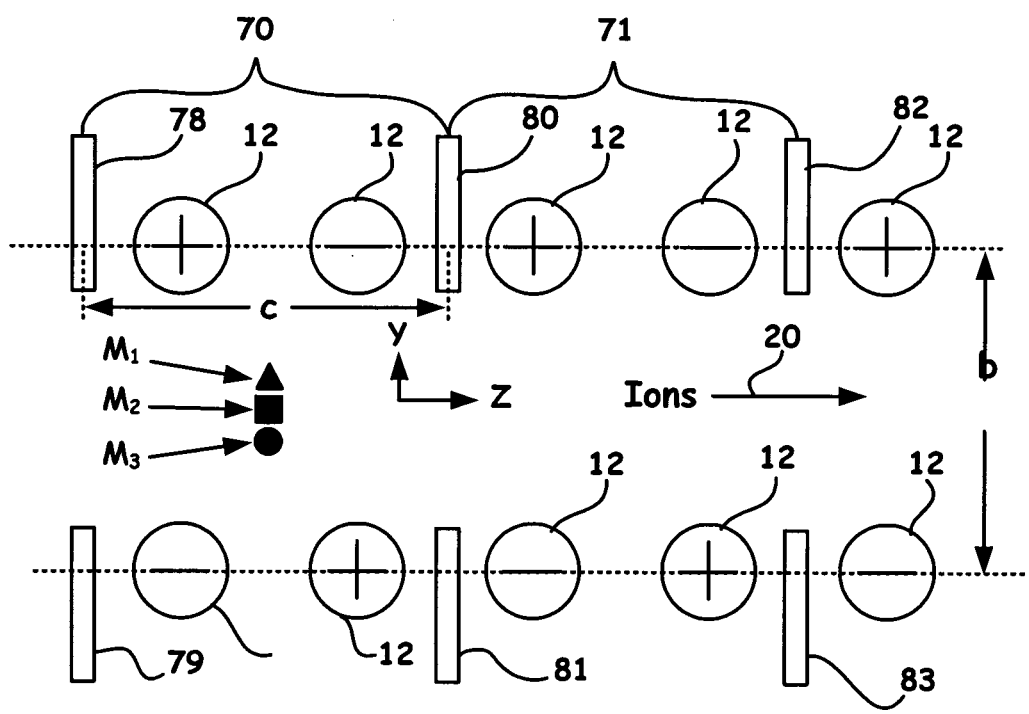
FIG. 3B shows another example embodiment for designed confinement channels configured within the 2D high ion storage/ion mobility confinement interface instrument.

FIG. 3B shows another example embodiment for designed confinement channels, as generally shown by the 2D high ion storage/ion mobility confinement interface instrument 14 in FIG. 1. As stated above, the configurations detailed in FIG. 2A and FIG. 2B reflect a design that entails a single confinement channel along the Z-axis provided as defined by the 2X inter-rod distance "a", as discussed above. FIG. 3B, by contradistinction, shows an arrangement wherein the confinement channels comprise a distance now labeled as "c", (e.g., as defined by auxiliary electrode distances as also denoted by the accompanying bi-directional arrows shown in FIG. 3B).

In contradistinction to or in addition to the arrangements described above with respect to the example embodiments of FIG. 2A and FIG. 2B, the confinement channel regions (two example regions denoted as 70 and 71) are now capable of being configured with disposed one or more auxiliary electrodes, e.g., 78, 79, 80, 81, 82, and 83, between respective RF electrodes 12 so as to enable required DC potentials to be adjusted for channel confinement of desired ions (e.g., via high potentials at predetermined auxiliary electrodes).

In addition, applied confinement DC potentials to such auxiliary electrodes, e.g., 78, 79, 80, 81, 82, and 83, can also be removed to eliminate potential barriers between one or more confinement regions (e.g., 70 and 71) and adjusted (to enable an applied DC gradient of about 1 V/cm up to about 10 V/cm) in order to enable ion mobility transport and separation of desired ions into any one of designed confinement channels.

In operation, ions having different m/z values, e.g., generally labeled as $M_1$, $M_2$, and $M_3$ (again shown respectively as a triangle, square and circle) generated by ion source 2 (e.g., an ESI source) can be directed via ion transfer optics 4 (e.g., an aperture ion lens) so as to, as stated above, fill Region I 16 of the 2D high ion storage/ion mobility confinement interface instrument 14 up to its limit (e.g., $N*C_T$). As also stated hereinbefore, gas (e.g., Helium, Neon, Argon) pressure of about 20 mtorr up to about 0.1 torr can fill the confinement regions where desired to enable ion mobility transport without causing deleterious fragmentation effects while acting in cooperation with applied DC gradients.

As before, using controllers and applicable DC and RF power supplies, repulsive RF and/or DC voltages to electrode structures known by those skilled in the art (end plates, aperture lenses, etc.), are employed at opposing ends of each confinement channel or at segmented portions to keep ions within the interior of the long axis of the electrode 12 structures.

While a schematic representation of applied DC potentials is not shown in FIG. 3B, once a desired number of ions within a given mass range have been evenly distributed at up to the limit (e.g., $N*C_T$) into Region I, as discussed above, and confined in a configured DC potential well via applied DC voltages to, as an example only, to predetermined one or more auxiliary electrodes, e.g., 78, 79, 80, and 81, such potentials can be removed and DC pulses in the tens of microseconds can thereafter be applied to predetermined auxiliary electrodes, e.g., 78, 79, 80, 81, 82, and 83 to enable a desired DC electric field gradient of about 1 V/cm up to about 10 V/cm. The applied RF field (not indicated) working in cooperation with the applied DC gradient and gas pressure aids the ions (e.g., $M_1$, $M_2$, and $M_3$) to move substantially in the transverse direction 20 via ion mobility transport principles.

Once the separation is completed, ions (e.g., $M_1$, $M_2$, and $M_3$) can be locked into corresponding confinement channels (e.g., 71) via configured DC potential wells by raising the DC fields at selected electrodes (e.g., 80, 81, 82, and 83) in a predetermined fashion. Upon separation, example ions $M_1$, $M_2$, and $M_3$ can be ejected, as before along the long axis of each confinement cell and into Region III 31 of mass spectrometer system 100 using applied DC potentials (e.g., using opposing DC end plates and aperture lenses) or DC gradients enabled by configured auxiliary electrodes 28, as shown by the dashed lines in FIG. 1, and or the auxiliary electrodes, e.g., 78, 79, 80, 81, 82, and 83, as shown in FIG. 3B.

It is to be appreciated that the example auxiliary electrodes 78, 79, 80, 81, 82, and 83 can also be configured with one or more finger electrodes, as described in U.S. Pat. No. 7,675,031 and as incorporated by reference herein, so as to be disposed between predetermined pairs of main rod electrodes 12, as generally shown in FIG. 3B. The relative positioning of the auxiliary electrodes 54, 55, 56, 57 with respect to the main RF rod electrodes 12 can be at about equal distances from the main RF electrodes of the multipole ion guide device where the quadrupolar fields are substantially zero or close to zero so as to minimize interference with the quadrupolar fields.

If configured with a beneficial array of finger electrodes (not shown), a voltage applied to the array of finger electrodes can also create an axial electric field along the long direction of the electrodes 12 in the interior of the ion guides. Moreover, such arrays can also be provided with desired resistors to enable respective voltage dividers along lengths of the auxiliary electrodes e.g., 78, 79, 80, 81, 82, and 83, as shown in FIG. 3B. The resultant voltages can thus form a range of voltages, often a range of step-wise monotonic voltages to create a voltage gradient in the long electrode direction that urges ions so as to be similarly directed to Region III 31 while a new set of ions (e.g., new $M_1$, $M_2$, and $M_3$ ions) continue to fill Region I 16 of the high duty cycle ion storage/ion mobility mass spectrometer system 100, as shown in FIG. 1.

Once directed to Region III 31 from embodiments discussed above, the confinement of predetermined ions 36 into individual confinement channels of smaller mass ranges can similarly be achieved, as stated above, by the combined action of oscillatory (e.g., RF) and static fields effected by the application of desired voltages (RF and DC) to electrodes 32 of Region III 31. Confinement along the long axis of electrodes 32 that provide confinement channels, as before, is enabled by repulsive DC and RF potentials applied to known electrode structures in the field of mass spectroscopy. When transfer of ions is desired, certain voltages are adjusted or removed to the main RF electrodes 32 in order to eliminate potential barriers between adjacent confinement regions so as to urge ions to the next confinement cell so as to be eventually received by the aforementioned analyzer 40. Axial DC fields can also be applied to urge ions towards the analyzer 40 in the transverse direction. The result, as before, is a data 42 having a desired spectral quality due to the increase in dynamic range provided by the mass spectrometer 100 of FIG. 1.

To aid the reader in understanding the possible various embodiments of the present invention, the following example is provided for reference when considering designing the 2D high ion storage/ion mobility confinement interface instrument portion of the mass spectrometer system described herein, which is intended to be illustrative only, but not limiting thereof.

EXAMPLE

As stated above, there is an inherent limit ($N*C_T$) to the number of ions capable of filling a designed ion storage section, such as, in this case, the confinement channels labeled Region II 18 in FIG. 1 and FIG. 2A and is instrumental when considering designing the mass spectrometer 100 of FIG. 1. It is to be appreciated that Region II 18, as shown in FIG. 1, is a configured number of desired channels, e.g., 12-20 ion storage confinement cells, as enabled by prescribed pairs of elongated electrodes 12. In an example case of 16 confinement channels 13 to store a mass range of for example, about 400 amu up to about 1400 amu, each channel 13 within Region II 18, as shown in FIG. 1, occupies in this example scenario, a mass range of about 60 AMU, i.e., (1400-400 AMU/16 channels)~60 AMU/channels. In consideration for the design geometry along the Z-axis for Region II 18, each channel 13, occupies a physical space of two inter-rod distances, i.e., a 2× inter-rod separation distance "a", as shown in FIG. 2B, as discussed above. If an inter-rod beneficial separation distance is, for example, about 3 millimeters (mm) from center to center, the 2× inter-rod separation distance "a" is about 6 mm in distance. Accordingly, for this example, 16 desired confinement channels is about 96 mm in length along the Z-axis (i.e., 6 mm*16 confinement channel=96 mm). This length, i.e., $L_2-L_1$ (as shown at the top of FIG. 2A) corresponds to the linear dimension of Region II that desired ions of one or more sub-regions of an overall mass range must travel in a give time frame via ion mobility separation means.

In defining a length of travel Lq along the 2D ion storage/ion mobility instrument 14, $$L_1 = v_1 * t = K_1 * E * t = \frac{\alpha_0}{\Omega_1} * E * t, \text{ and} \qquad 1)$$

$$L_2 = v_2 * t = K_2 * E * t = \frac{\alpha_0}{\Omega_2} * E * t, \qquad 2)$$

wherein t relates to the travel or ion mobility separation time, E relates to the electric field strength in volts per centimeter (V/cm). K, in particular relates to the ion mobility factor that in a predetermined electric field (E) depends on the ion/buffer gas cross-section $\Omega$ in Angstroms² (Å²), and $\alpha$ (p,T,m)=$\alpha_o$, which is factor dependent on buffer gas (m), pressure (p) and temperature (T). This allows a spatial separation of ions, including structural isomers.

The reader is now directed to FIG. 3A, which shows the relationship between the collision cross-section measurements $\Omega$ (Å²) of singly 62 and doubly 66 protonated proteins as a function of molecular weight (MW) (see Valentine, S. J., Counterman, A. E., Clemmer, D. E., J. Am. Soc. Mass Spectrom. 1999, 10: 1188-1211). In particular, FIG. 3A shows a strong correlation of increasing cross section with increasing molecular weight. Accordingly, knowing a given mass range, e.g., 400 amu to about 1400 amu (which is an example m/z range typical for proteomics) to be spread out sequentially in a number of predetermined confinement channels (e.g., 16), one can derive correlated respective cross sections at the ends of a predetermined mass spectrum from the example plot of FIG. 3A, e.g., $\Omega$ (400 amu)=$\Omega_1$~120 Å², and $\Omega$ (1400 amu) =$\Omega_2$~300 Å². The cross section of $\Omega_2$~300 Å² for 1400 amu can be used in the design for Region II ($L_2-L_1$) as the ions of the end of the mass spectrum are desirably chosen to be contained at the front end of the plurality of confinement channels. However, Region I ($L_1$)) comprises the entire mass range prior to separation via ion mobility transport and thus the average cross section $\Omega$ (Ave) within Region I for the mass range is utilized and for this example is given by equation (3):

$$\Omega(Ave)=\Omega_2*\Omega_1/\Omega_2-\Omega_1=(300 \text{ Å}^2*120 \text{ Å}^2)/(300 \text{ Å}^2-120 \text{ Å}^2)=200 \text{ Å}^2. \qquad 3)$$

Accordingly, with respect to FIG. 2A, the ratio of Region I=$L_1$=($\alpha_o$Et)/$\Omega_1$ and Region II=$L_2-L_1$=($\alpha_o$Et)/$\Omega$(Ave) results in the ratio of cross-sectional areas to provide a percentage of the two regions, as shown by equation (4):

$$\frac{L_1}{L_2-L_1} = \frac{\Omega_{AVE}}{\Omega_2} = \frac{200}{300} = 0.67 \qquad 4)$$

Therefore, in this example, because a designer of the present invention is given that $L_2-L_1$=96 mm, the given mass range and thus the derived cross-section measurements, equation (4) shown above, enables one to derive the length of Region I ($L_1$), i.e., (96 mm*(0.67)=64 mm=$L_1$. In speaking to this example configuration, because $L_2-L_1$=96 mm, the total length for $L_1$+($L_2-L_1$)=64 mm+96 mm=160 mm=approximate physical length of an example ion interface/ion mobility instrument to be utilized herein.

Next, it is to be appreciated that the fill time for the 2D high ion storage/ion mobility confinement interface instrument 14 that comprises labeled storage Regions I 16 and II 18, as shown in FIG. 1, is given by equation (5):

Fill Time (sec)=(Ion Trap Capacity ($C_T$))/Ion source Flux*# of channels (N). 5)

Using the above example 16 confinement channels as the configuration without limiting the present invention to such an arrangement, if the example ion source is an ESI ion source (a high brightness ESI ion source) capable of generating an ion flux of about 5*10⁸ ions/sec, of which corresponds to an ion trap limit $C_T$ of about 5*10⁵ ions, then the fill time correspond in this example to:

Fill Time=5*10⁵ ions/5*10⁸ ions/sec*16=16 msec. 6)

Using a beneficial scan time for a mass spectrometer of about 15 μsec/amu and the example 1000 amu mass range of above (e.g., (400-1400 amu), results in a example scan time of the system 100 of FIG. 1 of:

Scan Time=15 μsec/AMU*1000 AMU=15 μsec. 7)

The difference in time between equations 6 and 7 above indicates that for this example embodiment, 1 msec is provided for transport and separation along Region II 18 of the instrument shown in FIG. 1 as well as for transport along Region III 31 so as to be collected and interrogated by analyzer 40, 40', etc. It is to be next appreciated that for this non-limiting example, one then adjusts the applied electric field (E) and t such that separation occurs in Region II 18 at times much less than 1 msec so as to also be collected in a reasonable time frame by Region III 31 for transfer to mass analyzer 40. In particular, this means (E) and t are chosen such that ions of 1400 m/z travel the aforementioned 96 mm along Region II (i.e., the length of $L_2-L_1$) in less than 1 msec, beneficially for example, within about 200 μsecs. For the example model herein of a cross-section of $\Omega_2$~300 Å², and with a pressure of about 100 mtorr, a resultant example E-field is about 4.0 V/cm to enable the desired ions to travel the 96 mm in 197 μsecs. The total voltage drop across is about 107 volts. It is to be noted that for fragile components, total separation time may be increased by 4× by reducing the field strength, e.g., down to about 1.0 V/cm for this example. Resultant from example configurations provided herein, applied DC fields and gas pressures enable ion mobility resolutions of about 10.

It is to be understood that features described with regard to the various embodiments herein may be mixed and matched in any combination without departing from the spirit and scope of the invention. Although different selected embodiments have been illustrated and described in detail, it is to be appreciated that they are exemplary, and that a variety of substitutions and alterations are possible without departing from the spirit and scope of the present invention.

The invention claimed is:

1. A high duty cycle ion storage/ion mobility mass spectrometer, comprising:
an ion source;
a first ion interface instrument partitioned into a first region and a second region so as to be configured as a two-dimensional (2D) plurality of sequentially arranged confinement channels having predetermined spatial locations provided by desired DC and RF potentials, wherein a first confinement channel of said first region is configured to receive ions of a predetermined mass window from said ion source and one or more confinement channels ($N_1$) configured within said second region is designed, via ion mobility transport, to receive and thereafter confine selected ions of a smaller fraction of the mass range of said predetermined mass window once a desired number of ions within a given mass range have been evenly distributed into said first region;
a second ion interface instrument additionally partitioned into a (2D) plurality of sequentially arranged confinement channels ($N_2$) also having predetermined spatial locations provided by desired DC and RF potentials, wherein any of said (2D) plurality of sequentially arranged confinement channels ($N_2$) is configured to transversely receive selected ions of a smaller fraction of the mass range of said predetermined mass window from said one or more confinement channels ($N_1$) configured within said second region of said first ion interface instrument, said second ion interface instrument being additionally configured to transfer such selected ions to successive ion confinement channels; and
one or more mass analyzers having an entrance configured to receive ions transferred from one or more predetermined confinement channels of said second ion interface instrument to enable high throughput mass analysis.

2. The mass spectrometer of claim 1, wherein said two-dimensional (2D) plurality of sequentially arranged confinement channels ($N_1$) of said second region of said first ion interface instrument and said (2D) plurality of sequentially arranged confinement channels ($N_2$) of said second ion interface instrument comprises about 12 confinement channels up to about 20 confinement channels.

3. The mass spectrometer of claim 1, wherein said mass spectrometer is configured with electrodes selected from: one or more auxiliary electrodes, plate electrodes, and predetermined multipole electrodes to provide DC confining potentials and DC axial gradients.

4. The mass spectrometer of claim 3, wherein said one or more auxiliary electrodes, plate electrodes, and predetermined multipole electrodes are configured to provide a DC gradient of about 1 V/cm up to about 10 V/cm to aid ion mobility transport and separation.

5. The mass spectrometer of claim 3, wherein said one or more auxiliary electrodes are configured within said first ion interface instrument to provide transfer to said second ion transfer instrument.

6. The mass spectrometer of claim 1, wherein said confinement channels of said mass spectrometer are configured with gas pressures of about 20 mtorr up to about 100 mtorr.

7. The mass spectrometer of claim 1, wherein said mass spectrometer comprises a controller coupled to said ion source and said first and said second ion interface instruments to apply predetermined confining voltages and sufficient gradient voltages to aid ion mobility transfer and separation.

8. The mass spectrometer of claim 1, wherein said ion source comprises at least one source selected from: an Electrospray Ionization (ESI) source, an Atmospheric Pressure Ionization (API) source, an Atmospheric Pressure Chemical Ionization (APCI) source, a Nanoelectrospray Ionization (NanoESI) source, a thermospray ionization source, an electron impact (EI) ionization source, a chemical ionization (CI) source, and an EI/CI source.

9. The mass spectrometer of claim 1, wherein said one or more mass analyzers comprises at least one analyzer selected from: quadrupole mass analyzers, a two-dimensional ion trap, a three dimensional ion trap, an electrostatic trap, a time-of-flight (TOF) device, and a Fourier Transform Ion Cyclotron Resonance analyzer.

10. A method of mass spectrometric analysis, comprising:
a) providing an ion interface instrument partitioned into a first region and a second region so as to be configured as a two-dimensional (2D) plurality of sequentially arranged confinement channels, each of which has predetermined fixed spatial locations configured from desired DC and RF potentials,
b) providing a packet of ions of a predetermined mass window into a first confinement channel within said first region;
c) releasing ions of said predetermined mass window from said first confinement channel within said first region once a desired number of ions within a given mass range have been evenly distributed into said first region and locking fractions of said desired ions into predetermined one or more confinement channels ($N_1$) configured within said second region after urging, via ion mobility separation and transport, into said predetermined one or more confinement channels ($N_1$);
d) providing a subsequent packet of ions of said predetermined mass window into said first confinement channel after the transfer of said fractions of said ions of said predetermined mass window into said one or more confinement channels ($N_1$) configured within said second region;
e) transferring one or more of more of said fractions of ions of said predetermined mass window to an entrance of one or more mass analyzers;
f) mass analyzing said ions of said predetermined mass window;
g) repeating steps c) to f); for any number of a plurality of said subsequent packet of ions of a predetermined mass window, wherein said packet of ions have a mass-to-charge window similar to a mass-to-charge window of any of said subsequent packet of ions.

11. The method of claim 10, wherein the transferring step e) further comprises:
e1) providing a second ion interface instrument additionally partitioned into a (2D) plurality of sequentially arranged confinement channels ($N_2$) also having predetermined fixed spatial locations provided by desired DC and RF potentials; and
e2) transversely receiving into any of said (2D) plurality of sequentially arranged confinement channels ($N_2$) of said second ion interface instrument, one or more of said fractions of said ions of said predetermined mass window from said one or more confinement channels ($N_1$) of said ion interface instrument; wherein said one or more of more of said fractions of said predetermined mass window are thereafter transferred to an entrance of said one or more mass analyzers.

12. The method of claim 11, wherein said receiving step e2) further comprises: fragmenting said fractions of said ions of said predetermined mass window prior to being received by any of said (2D) plurality of sequentially arranged confinement channels ($N_2$) of said second ion interface instrument.

13. The method of claim 11, wherein the maximum ion mobility transfer period of ions across the length of said partitioned (2D) plurality of sequentially arranged confinement channels ($N_1$) of said second region and the length of said partitioned (2D) plurality of sequentially arranged confinement channels ($N_2$) of said second ion interface instrument is set to a time frame that is less than the difference between the fill time for said first confinement channel of said first ion interface instrument and the scanning time for said predetermined mass window using a beneficial mass analyzer.

14. The method of claim 13, wherein an applied electric field (E) gradient and ion mobility separation time t are adjusted to provide said ion mobility transfer period.

15. The method of claim 14, wherein said applied electric field (E) gradient is enabled by a controller to provide DC pulses from about 1 microsecond (μsec) up to about 10 microseconds (μsecs).

16. The method of claim 14, wherein said applied electric field (E) gradient is enabled by a controller to provide DC pulses from about 10 microseconds (μsec) up to about 40 microseconds (psecs).

17. The method of claim 14, wherein said method further comprises: configuring electrodes to provide a DC gradient of about 1 V/cm up to about 10 V/cm so as to aid said ion mobility transport and separation are selected from: one or more auxiliary electrodes, a plate electrode, and multipole electrodes.

18. The method of claim 10, wherein said method further comprises: providing gas pressures of about 20 mtorr up to about 100 motor to aid said ion mobility transport and separation.

19. The method of claim 10, wherein said method further comprises: providing a mobility resolution of down to about 10.

20. The method of claim 10, wherein the step of transferring one or more of more of said fractions of ions of said predetermined mass window to an entrance of one or more mass analyzers further comprises Automatic Gain Control (AGC).

* * * * *